(12) United States Patent
Meier et al.

(10) Patent No.: US 10,278,651 B2
(45) Date of Patent: May 7, 2019

(54) EARLY CONFIRMATION OF A PROLONGED APERIODIC MEASUREMENT

(71) Applicant: KONINKLIJKE PHILIPS N.V., Eindhoven (NL)

(72) Inventors: Wilhelm Meier, Herrenberg (DE); Harald Greiner, Nufringen (DE); Thomas Gerhard Emmrich, Gaertringen (DE); Steffen Zimmermann, Dettenhausen (DE)

(73) Assignee: KININKLIJKE PHILIPS N.V., Eindhoven (NL)

( * ) Notice: Subject to any disclaimer, the term of this patent is extended or adjusted under 35 U.S.C. 154(b) by 193 days.

(21) Appl. No.: 14/894,016

(22) PCT Filed: Jun. 18, 2014

(86) PCT No.: PCT/IB2014/062318
§ 371 (c)(1),
(2) Date: Nov. 25, 2015

(87) PCT Pub. No.: WO2014/207609
PCT Pub. Date: Dec. 31, 2014

(65) Prior Publication Data
US 2016/0128644 A1 May 12, 2016

Related U.S. Application Data

(60) Provisional application No. 61/838,376, filed on Jun. 24, 2013.

(51) Int. Cl.
*A61B 5/00* (2006.01)
*G06F 19/00* (2018.01)
(Continued)

(52) U.S. Cl.
CPC ............ *A61B 5/743* (2013.01); *A61B 5/7285* (2013.01); *A61B 5/742* (2013.01); *A61B 5/7475* (2013.01);
(Continued)

(58) Field of Classification Search
CPC ........ A61B 5/743; A61B 5/7285; A61B 5/742
See application file for complete search history.

(56) References Cited

U.S. PATENT DOCUMENTS 6,083,156 A * 7/2000 Lisiecki ............. A61B 5/02055
600/301
8,075,509 B2 12/2011 Molducci et al.
(Continued)

FOREIGN PATENT DOCUMENTS

| EP | 1249691 | 10/2002 |
|---|---|---|
| JP | 2006255020 | 9/2006 |

(Continued)

*Primary Examiner* — Omar R Abdul-Ali

(57) ABSTRACT

A medical device (10), medical method and graphical user interface (GUI) (18) displaying data regarding measurement of a physiological parameter. A window (22) for the physiological parameter is displayed using a display device (20). The window (22) includes an indicator (24) identifying a measured value of the physiological parameter. In response to automatic trigger of measurement of the physiological parameter, the window (22) is updated to further include a first indicator (34) indicating measurement of the physiological parameter is ongoing. In response to manual trigger of measurement of the physiological parameter, the window (22) is updated to replace the indicator (24) identifying the measured value with a second indicator (36) indicating measurement of the physiological parameter is ongoing. The second indicator (36) is prominent relative to the first indicator (34).

20 Claims, 4 Drawing Sheets

(51) Int. Cl.
 *A61B 5/01* (2006.01)
 *A61B 5/021* (2006.01)
 *A61B 5/022* (2006.01)
 *A61B 5/08* (2006.01)

(52) U.S. Cl.
 CPC ............... G06F 19/00 (2013.01); *A61B 5/01* (2013.01); *A61B 5/021* (2013.01); *A61B 5/022* (2013.01); *A61B 5/0816* (2013.01); *A61B 5/7435* (2013.01)

(56) References Cited

U.S. PATENT DOCUMENTS

| | | | | |
|---|---|---|---|---|
| 2005/0222873 | A1* | 10/2005 | Nephin | A61B 5/0205 705/2 |
| 2008/0300572 | A1* | 12/2008 | Rankers | A61B 5/14532 604/504 |
| 2010/0094096 | A1 | 4/2010 | Petruzzelli | |
| 2011/0071420 | A1 | 3/2011 | St. Pierre et al. | |
| 2011/0279469 | A1* | 11/2011 | Hao | G06Q 10/06 345/582 |
| 2013/0267792 | A1* | 10/2013 | Petersen | G06F 19/3418 600/301 |
| 2014/0275818 | A1* | 9/2014 | Kassem | A61B 5/746 600/301 |

FOREIGN PATENT DOCUMENTS

| | | |
|---|---|---|
| WO | 2006/076498 | 7/2006 |
| WO | 2010/126916 | 11/2010 |

* cited by examiner

EARLY CONFIRMATION OF A PROLONGED APERIODIC MEASUREMENT

CROSS REFERENCE TO RELATED APPLICATIONS

This application is a national filing of PCT application Serial No. PCT/IB2014/062318, filed Jun. 18, 2014, published as WO 2014/207609 on Dec. 31, 2014, which claims the benefit of U.S. Provisional Application No. 61/838,376 filed Jun. 24, 2013, all of which are incorporated herein by reference.

The present application relates generally to patient monitoring. It finds particular application in conjunction with prolonged aperiodic measurements, and will be described with particular reference thereto. However, it is to be understood that it also finds application in other usage scenarios and is not necessarily limited to the aforementioned application.

Measurements can be continuous or aperiodic. Aperiodic measurements can be started and/or triggered manually and/or automatically (e.g., repetitively for a specific interval or controlled via a specified time sequence). Some aperiodic measurements take a prolonged time to complete (i.e., not just seconds, but sometimes a fraction of a minute to multiple minutes). During this measurement time, some measurements continually derive and update an estimated measurement value, which usually gets better as more time passes. Once certain criteria are met, the measurement terminates and the estimated measurement value is provided as a final measurement value. These criteria can include the estimated measurement value becoming stable or a certain quality (e.g., accuracy) being achieved.

In known systems, while a measurement is ongoing, either: A) the previously measured value, including its timestamp, is kept on the display and a subtle indication (e.g., a dot next to the previously measured value) is used to indicate that a measurement is ongoing; or B) the previously measured value, including its timestamp, is removed from the display and that space is used for a prominent indication that the measurement is ongoing (e.g., a sequence of moving dashes). These two approaches to indicating a measurement is ongoing pose a number of challenges, especially for prolonged measurements.

A challenge with the first approach to indicating that a measurement is ongoing (i.e., Approach A) is that a user that manually starts a measurement does not get clear feedback that the measurement started and is still is ongoing. The user may conclude that the measurement failed to start by failing to observe the subtle indicator and observing the "old" timestamp. By concluding that the measurement failed to start, the user may potentially stop the measurement inadvertently (e.g., by again pushing a toggle button that was initially pushed to start the measurement) or record the previous measured value. This challenge is exacerbated by less trained users, more prolonged measurements, and measurements that do not provide any other obvious cue that they are still ongoing (e.g., a pump and cuff used for measuring noninvasive blood pressure (NBP) gives an obvious cue).

A challenge with the second approach to indicating that a measurement is ongoing (i.e., Approach B) is that a user who wants to check and/or record the value of a measurement that was triggered automatically may try to do so when a new measurement is triggered automatically and still ongoing. The user then has to wait, potentially a considerable time, until that measurement is done. The more frequently a measurement is triggered and the longer such a measurement takes, the more burdensome to the user such a behavior becomes.

The present application provides a new and improved system and method which overcome the above-referenced problems and others.

In accordance with one aspect, a medical device displaying data regarding measurement of a physiological parameter is provided. The medical device includes a display device and at least one processor. The at least one processor is programmed to display a window for the physiological parameter using the display device. The window includes an indicator identifying a measured value of the physiological parameter. The at least one processor is further programmed to, in response to an automatic trigger of measurement of the physiological parameter, update the window to further include a first indicator indicating measurement of the physiological parameter is ongoing. Even more, the at least one processor is programmed to, in response to a manual trigger of measurement of the physiological parameter, update the window to replace the indicator identifying the measured value with a second indicator indicating measurement of the physiological parameter is ongoing. The second indicator is prominent relative to the first indicator. For example the second indicator is dynamic over time and the first indicator is static over time or the second indicator is displayed with a larger size than the first indicator, or both.

In accordance with another aspect, a medical method displaying data regarding measurement of a physiological parameter is provided. A window for the physiological parameter is displayed using a display device. The window includes an indicator identifying a measured value of the physiological parameter. In response to automatic trigger of measurement of the physiological parameter, the window is updated to further include a first indicator indicating measurement of the physiological parameter is ongoing. In response to manual trigger of measurement of the physiological parameter, the window is updated to replace the indicator identifying the measured value with a second indicator indicating measurement of the physiological parameter is ongoing. The second indicator is prominent relative to the first indicator. For example the second indicator is dynamic over time and the first indicator is static over time or the second indicator is displayed with a larger size than the first indicator, or both.

In accordance with another aspect, a graphical user interface (GUI) displaying data regarding measurement of a physiological parameter is provided. The GUI includes a window for the physiological parameter displayed using a display device. The window includes an indicator identifying a measured value of the physiological parameter. The window is updated to further include a first indicator indicating measurement of the physiological parameter is ongoing in response to automatic trigger of measurement of the physiological parameter. The window is updated to replace the indicator identifying the measured value with a second indicator indicating measurement of the physiological parameter is ongoing in response to manual trigger of measurement of the physiological parameter.

One advantage resides in an improved display of automatic, manual and prolonged measurements.

Another advantage resides in improved clinician workflow.

Another advantage resides in an enhanced user interface giving clear and appropriate feedback dependent on whether a measurement is automatically or manually triggered.

Another advantage resides in reducing the potential for inadvertent user mistakes.

Another advantage resides in reducing the amount of time clinicians spend collecting vital sign measurements.

Still further advantages of the present invention will be appreciated by those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

FIG. 12 illustrates a display including an indicator indicating one or more of the progress of a measurement, the stability of an estimate of a parameter, a quality (e.g., accuracy) of the estimate, and the like.

The present invention proposes an approach for indicating that a measurement is ongoing. According to this approach, the previously measured value, including its timestamp, is kept on the display and a subtle indication, in a first format, (e.g., a dot next to the previously measured value, or another character or graphical symbol which is displayed in a smaller size relative to the size of the displayed measured value) is used to indicate that a measurement is ongoing for automatically triggered measurements. This effectively hides the long duration of the measurement. Further, according to this approach, the previously measured value, including its timestamp, is removed from the display and that space is used for a prominent indication, in a second format, that a measurement is ongoing (e.g., a sequence of moving dashes, a sequence of one or more characters that changes as a function of time, a sequence of graphic symbols that changes as a function of time, etc.) for manually triggered measurements.

Further, the present invention proposes an approach for enhancing the behavior of manually triggered measurements that take a prolonged time (i.e., not just seconds, but sometimes a fraction of a minute to multiple minute). This includes deriving and showing a preliminary value, as well as allowing a user to accept the preliminary value. The user can, for example, accept the preliminary value based on their clinical judgment and/or if the measurement algorithm, after an extended period of time, cannot reach an acceptable value (e.g., a good/stable value) and would otherwise abort the measurement indicating an inoperative state (INOP).

Figure 1:
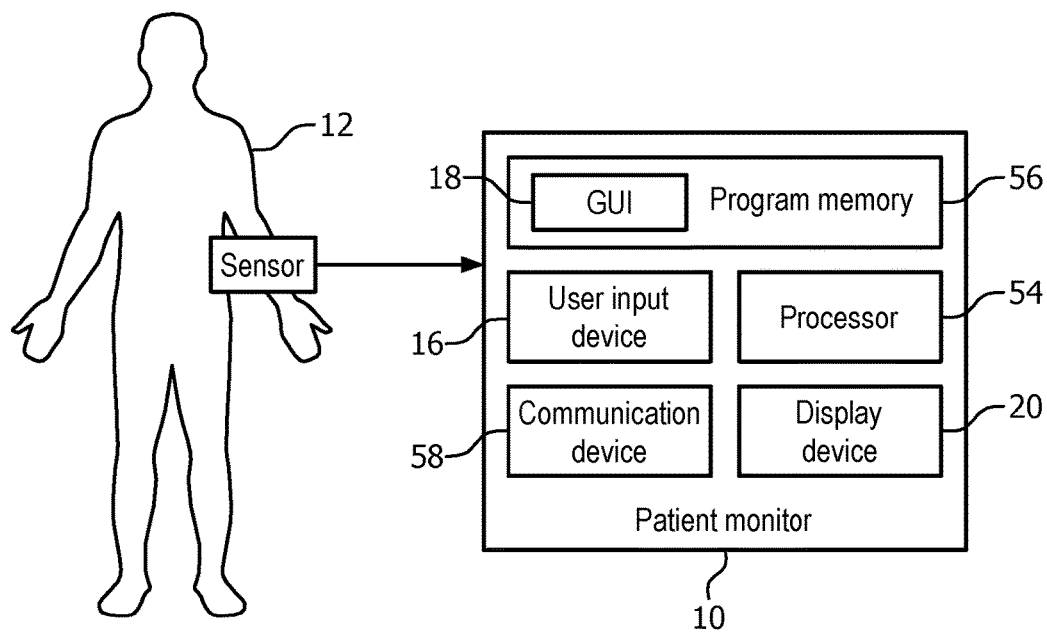
FIG. 1 illustrates a device with an enhanced graphical user interface (GUI) for displaying measurements.

With reference to FIG. 1, a device 10 for carry out the present invention is illustrated. The device 10 can be any electronic device capable of electronically displaying measured values of a parameter and which can either: 1) locally measure the parameter; or 2) communicate with a remote device and/or system measuring the parameter. The device 10 is typically a medical device, such as the illustrated patient monitor, a bedside monitor or other types of devices. Further, the parameter is typically a physiological parameter and/or vital sign of a person 12 requiring a prolonged period of time (i.e., more than a few seconds) to measure, but other parameters are contemplated. Such a physiological parameter can include, for example, respiration rate measured through motion, noninvasive blood pressure (NBP) and temperature.

Measurement of the parameter varies depending upon the type of parameter. For certain types of parameter, a measured value is determined by continuously refining an estimate of the parameter during the course of the measurement until completion of the measurement. Upon completion of the measurement, the estimate becomes the measured value. Measurement of the parameter can complete after predetermined criteria are achieved. Such predetermined criteria can include, for example, one or more of a predetermined amount of time passing since the measurement began, the estimate achieving a predetermined stability and/or a predetermined accuracy, and so on. Further, measurement of the parameter, regardless of type, can fail, such as when the predetermined criteria are not met within a predetermined amount of time.

Where the device 10 locally measures the parameter, the device 10 includes one or more sensors 14 used by the device 10 to measure the parameter. The device 10 processes raw data collected from the sensors 14 to determine measured values. The device 10 can trigger measurement of the parameter automatically based on predetermined criteria and/or in response to user input. As to the former, for example, the parameter can be measured according to a timing sequence, such as at a predetermined frequency (e.g., every 30 minutes). As to the latter, for example, the user can initialize measurement of the parameter using a user input device 16, such as a button, of the device 10. As illustrated, the device 10 is a patient monitor locally measuring a physiological parameter of a patient using a sensor positioned on the patient's arm. The sensor could, for example, include a pump and cuff measuring NBP of the patient.

In some embodiments, the device 10 generates one or more preliminary values over the course of a measurement of the parameter. A preliminary value corresponds to an estimate of the parameter. Typically, a preliminary value is generated once the estimate achieves predetermined criteria, such as a predetermined degree of stability and/or a predetermined accuracy. The device 10 can additionally accept a preliminary value as the measured value and end measurement.

Where the device 10 communicates with the remote device and/or system measuring the parameter, the device 10 at least receives measured values from the external device and/or system. The device 10 additionally receives an event notification from the external device and/or system upon initialization of a measurement. This event notification indicates that measurement of the parameter has begun. Alternatively, the device 10 triggers the external device and/or system to measure the parameter automatically or in response to user input according to the same criteria described above. The device 10 additionally receives an event notification from the external device and/or system upon completion of a measurement. This event notification indicates that measurement of the parameter has completed and optionally includes the measured value.

In some embodiments, the device 10 receives one or more preliminary values over the course of a measurement of the parameter from the external device and/or system. As noted above, a preliminary value corresponds to an estimate of the parameter. Typically, a preliminary value is received once the estimate achieves predetermined criteria, such as a predetermined degree of stability and/or a predetermined accuracy. The device 10 can additionally accept a preliminary value as the measured value and/or end the measurement by the external device and/or system.

A graphical user interface (GUI) 18 of the device 10 displays graphical elements, such as icons, windows, menus, and so on, to a user on a display device 20 of the device 10. The graphical elements provide a user with a window 22 (see FIG. 2) indicating data regarding measurement of the parameter. The window 22 is any continuous region of the available screen space of the display device 20. The measurement data includes one or more of a measured value, when the measured value was determined, an identifier for the parameter, whether measurement of the parameter is automatically or manually triggered, the criteria for automatically triggering measurement of the parameter, whether a measurement of the parameter is ongoing, preliminary values, whether a measurement of the parameter failed, and the like. Further, the GUI 18 allows the user to manipulate and/or otherwise interact with the graphical elements using the user input device 16 of the device 10.

Figures 2, 3:
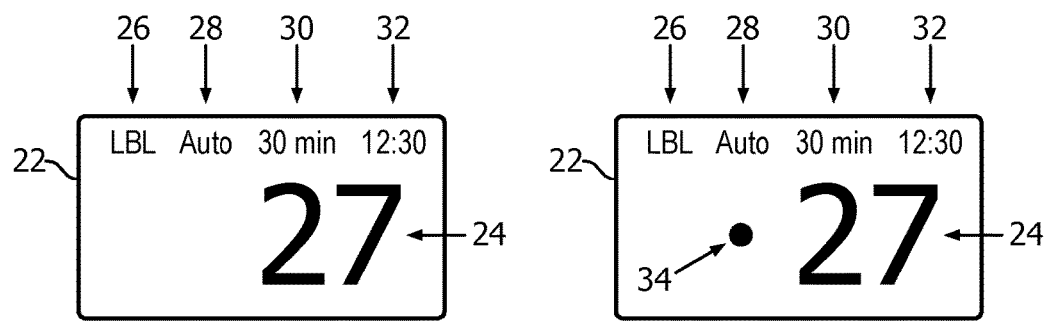
FIG. 2 illustrates a display after completing measurement of a parameter.
FIG. 3 illustrates a display while an automatically triggered measurement of a parameter is ongoing.

With reference to FIG. 2, upon completing measurement of the parameter, the window 22 of the GUI 18 includes an indicator 24 identifying the measured value, in this case 27. Further, the window 22 can include an indicator 26 identifying the parameter, in this case LBL. Even more, the window 22 can include an indicator 28 indicating whether the parameter is measured manually or automatically and an indicator 30 indicating when the parameter is automatically measured, such as a measurement frequency. As illustrated, the window 22 indicates the parameter is automatically measured every 30 minutes. Moreover, the window 22 can include an indicator 32 indicating when the measurement completed (i.e., a timestamp), in this case 12:30.

Indicators displayed upon completion of a measurement, described in connection with FIG. 2, differ from those displayed when a measurement is ongoing. Further, while a measurement is ongoing, the indicators displayed for a manually triggered measurement differ from those displayed for an automatically triggered measurement. However, regardless of the circumstances surrounding displayed indicators (e.g., regardless of whether a measurement is ongoing or not, and regardless of whether a measurement is manually or automatically triggered), displayed indicators can be text, graphics (e.g., icons), other like indicators, or any combination of the foregoing.

With reference to FIG. 3, when measurement of the parameter is automatically triggered (e.g., at a scheduled time), the indicator 24 identifying the previously measured value is kept on the window 22. Typically, one or more other indicators, such as the timestamp indicator 32, are also kept on the window 22. As illustrated, all of the indicators described in connection with FIG. 2 are kept on the window 22. Further, when measurement of the parameter is automatically triggered, a subtle indicator 34 can be displayed to indicate that a measurement is ongoing. The subtle indicator 34 corresponds to an indicator which does not draw the attention of a user. For example, the subtle indicator 34 is smaller in size than the indicator 24 identifying the previously measured value. Further, the subtle indicator 34 is typically static over time and adjacent the indicator 24 identifying the previously measured value, as illustrated. The subtle indicator 34 can, for example, be a dot, a dash, or the like.

With reference to FIGS. 4A-C and 5A-F, when measurement of the parameter is manually triggered by a user (e.g., a user selects the parameter from a menu of the GUI 18 using the user input device 16), the indicator 24 identifying the previously measured value is removed from the window 22. Typically, one or more other indicators, such as the timestamp indicator 32, are removed from the window 22. Further, when measurement of the parameter is manually triggered by a user, the window space previously used for the indicator 24 identifying the previously measured value is used for a prominent indicator 36 indicating that the measurement is ongoing. The prominent indicator 36 corresponds to an indicator which draws the attention of a user. For example, the prominent indicator 36 is prominent (i.e., more noticeable) relative to the subtle indicator 34. Further, the prominent indicator 36 is typically dynamic (e.g., changing according to a repeating sequence every predetermined amount of time, such as every 1 second) and comprised of, for example, dots, dashes, or the like. The prominent indicator 36 can distinguish from the subtle indicator 34 by using different formats, such as text size, color, shading, font, character, symbol, static or dynamic display, etc.

Figure 4A:
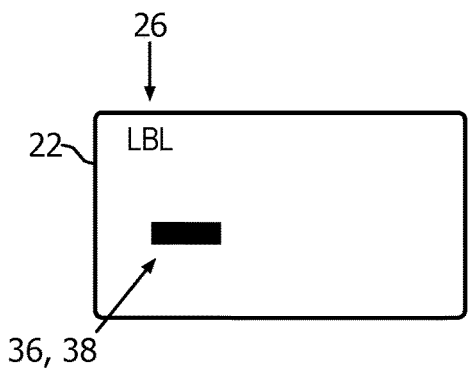
FIG. 4A illustrates a display while a manually triggered measurement of a parameter is ongoing, the display including a first element of a sequence indicating measurement is ongoing.
Figure 4B:
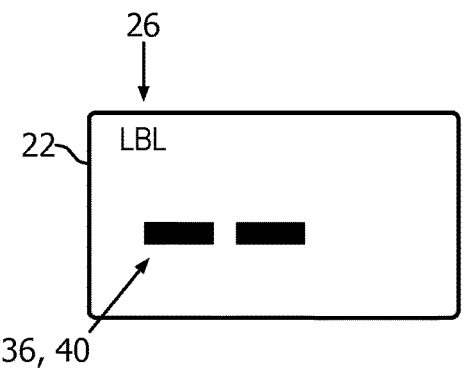
FIG. 4B illustrates a display while a manually triggered measurement of a parameter is ongoing, the display including a second element of a sequence indicating measurement is ongoing.
Figure 4C:
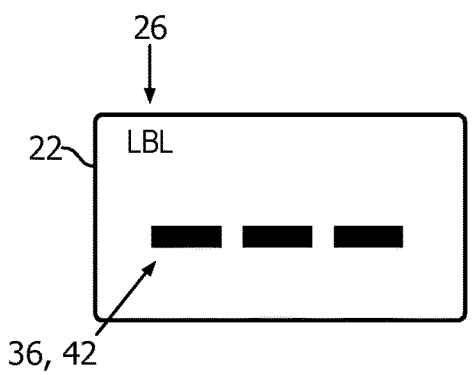
FIG. 4C illustrates a display while a manually triggered measurement of a parameter is ongoing, the display including a third element of a sequence indicating measurement is ongoing.
Figure 5A:
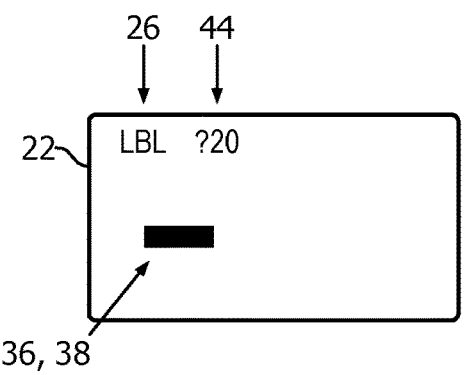
FIG. 5A illustrates a display while a manually triggered measurement of a parameter is ongoing, the display including a first element of a sequence indicating measurement is ongoing and an indicator indicating a preliminary value of 20.
Figure 5B:
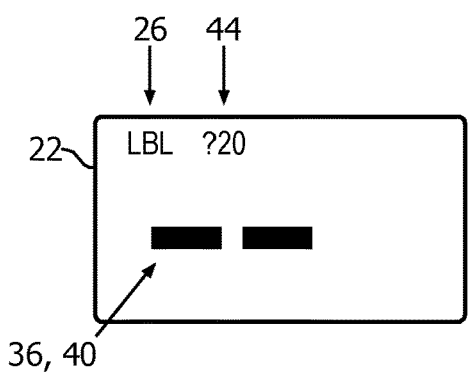
FIG. 5B illustrates a display while a manually triggered measurement of a parameter is ongoing, the display including a second element of a sequence indicating measurement is ongoing and an indicator indicating a preliminary value of 20.
Figure 5C:
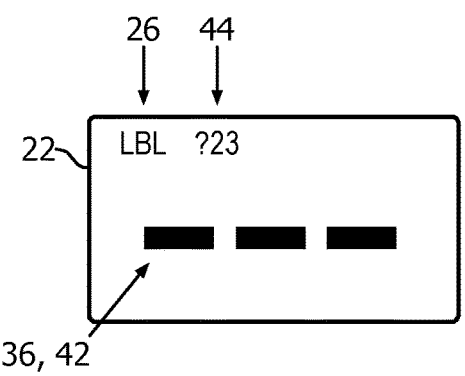
FIG. 5C illustrates a display while a manually triggered measurement of a parameter is ongoing, the display including a third element of a sequence indicating measurement is ongoing and an indicator indicating a preliminary value of 23.
Figure 5D:
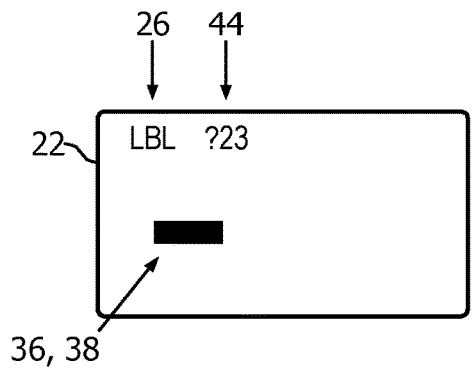
FIG. 5D illustrates a display while a manually triggered measurement of a parameter is ongoing, the display including a first element of a sequence indicating measurement is ongoing and an indicator indicating a preliminary value of 23.
Figure 5E:
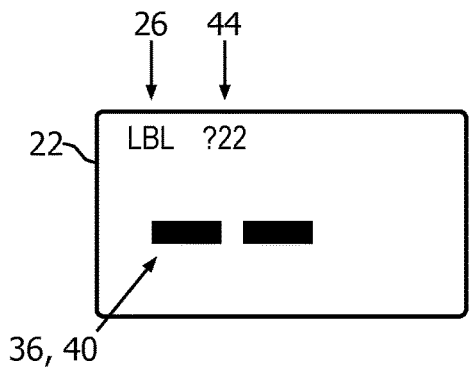
FIG. 5E illustrates a display while a manually triggered measurement of a parameter is ongoing, the display including a second element of a sequence indicating measurement is ongoing and an indicator indicating a preliminary value of 22.
Figure 5F:
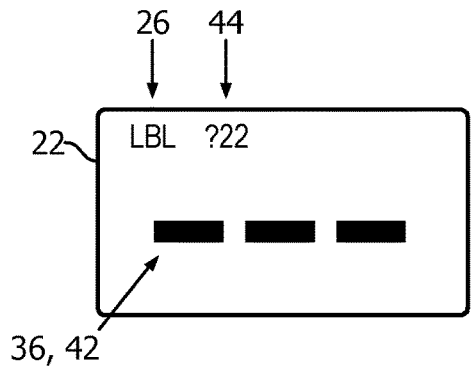
FIG. 5F illustrates a display while a manually triggered measurement of a parameter is ongoing, the display including a third element of a sequence indicating measurement is ongoing and an indicator indicating a preliminary value of 22.

As illustrated, the prominent indicator 36 is a repeating sequence of moving dashes. FIGS. 4A, 5A and 5D illustrate a first element 38 of the sequence comprised of a single dash. FIGS. 4B, 5B and 5E illustrate a second element 40 of the sequence comprised of two dashes and which follows the first element 38. FIGS. 4C, 5C and 5F illustrate a third element 42 of the sequence comprised of three dashes and which follows the second element 40. The first element 38 follows the third element 42. The time interval between each element can, for example, be 1 second. More or less elements are contemplated. Further, other prominent indicators are contemplated, such as dashes or dots marching in a line or rotating in a circle or the like.

With reference to FIGS. 4A-C, initially after manual triggering measurement of the parameter, all of the indicators described in connection with FIG. 2, except the indicator 26 identifying the parameter, can be removed from the window 22. Drawing upon the examples of the previous figures, measurement of the parameter could, for example, be manually triggered at 12:35 by a user of the device 10 using the user input device 16.

With reference to FIGS. 5A-F, an indicator 44 identifying a preliminary value can be displayed. As noted above, a preliminary value corresponds to an estimate of the parameter. The indicator 44 identifying the preliminary value can, for example, be text including a question mark or some other mark appended to the beginning or end of the preliminary value, where this mark identifies the preliminary value as "preliminary". During the course of a measurement, the indicator 44 identifying the preliminary value can be updated with newer preliminary values. For example, as illustrated in FIGS. 5A and 5B, the preliminary value of the indicator 44 may initially be 20. Sometime thereafter, as illustrated in FIGS. 5C and 5D, the preliminary value of the indicator 44 may be 23. Even more, sometime thereafter, as illustrated in FIGS. 5E and 5F, the preliminary value of the indicator 44 may be 22.

Figure 6:
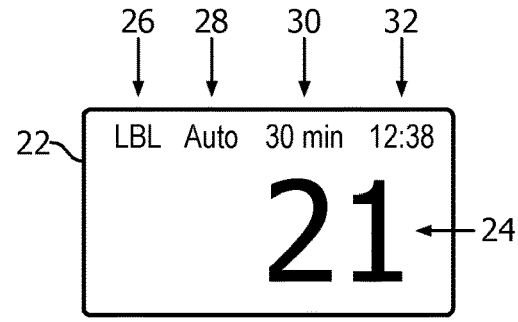
FIG. 6 illustrates a display after completing measurement of a parameter.

With reference to FIG. 6, when a measurement of the parameter completes, the prominent indicator 36 is replaced with the indicator 24 identifying the measured value, in this case 21. Further, the indicator 44 of the preliminary value is removed. The indicator 28 indicating whether the parameter is measured manually or automatically and the indicator 30 indicating when the parameter is automatically measured can be added to the window 22. Moreover, the indicator 32 indicating when the measurement completed, in this case 12:32, can be added to the window 22. A measurement completes after predetermined criteria are met. For example, a measurement completes when the estimate of the parameter reaches a sufficient accuracy and/or stabilizes.

Figure 7:
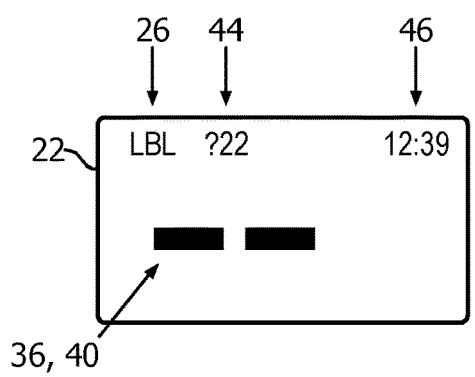
FIG. 7 illustrates a display after suspending measurement of a parameter due to failure to meet predetermined criteria.

With reference to FIG. 7, in some instances, a measurement may fail to meet the predetermined criteria after a maximum amount of time (e.g., 4 minutes) passes from initialization of the measurement. In this case, the device 10 ends the measurement and updates the window 22 to indicate the failure. This can be performed by updating the window 22 to include an indicator 46 indicating when the maximum amount of time was reached (i.e., a timestamp), in this case 12:39. Further, execution of the sequence of the prominent indicator 36 can be suspended so the prominent indicator 36 is static and the displayed element of the prominent indicator 36 at the time of the suspension persists.

Figure 8:
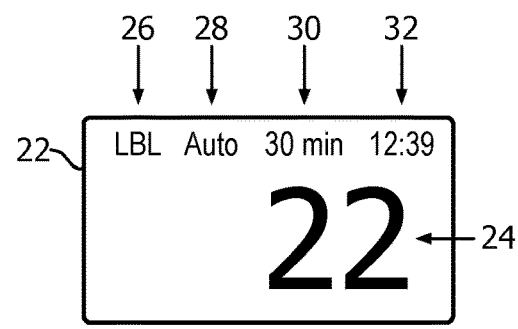
FIG. 8 illustrates a display after accepting a preliminary value while measurement of a parameter is suspended due to failure to meet predetermined criteria.

Upon ending the measurement and updating the window 22, a user has a predetermined amount of time (e.g., 2 minutes) to accept and/or confirm the preliminary value indicated on the window 22 using the user input device 16. For example, a user can select a menu item entitled "Accept preliminary value". An indicator, such as a progress bar, can be added to the window 22 to indicate the remaining time. With reference to FIG. 8, if the user accepts the preliminary value, in this case 22, the preliminary value becomes the measured value and the prominent indicator 36 is replaced with the indicator 24 identifying the measured value. Further, the indicator 28 indicating whether the parameter is measured manually or automatically, and/or the indicator 30 indicating when the parameter is automatically measured, can be added to the window 22. Even more, the indicator 44 identifying the preliminary value is removed. Moreover, the indicator 32 indicating when the measurement completed, in this case 12:39, can be added to the window 22.

Figure 9:
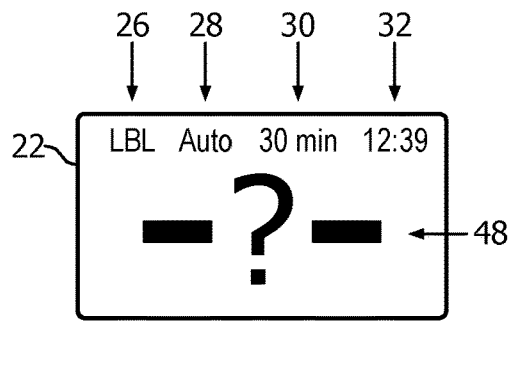
FIG. 9 illustrates a display after completing measurement of a parameter, where the measurement failed.

With reference to FIG. 9, if the user does not accept the preliminary value or fails to react within the predetermined amount of time, the measurement is aborted. Further, the prominent indicator 36 is replaced with an indicator 48 indicating the measurement was aborted, in this case a question mark. Even more, the indicator 28 indicating whether the parameter is measured manually or automatically, and/or the indicator 30 indicating when the parameter is automatically measured, can be added to the window 22. Moreover, the indicator 44 identifying the preliminary value is removed. Even more, the indicator 32 indicating when the measurement completed, in this case 12:39, can be added to the window 22.

Figure 10:
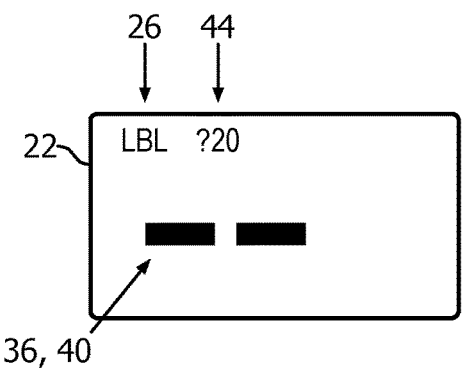
FIG. 10 illustrates a display while a measurement is ongoing.
Figure 11:
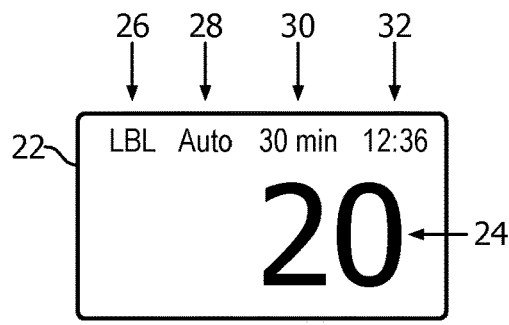
FIG. 11 illustrates a display after accepting a preliminary value while a measurement of a parameter is ongoing.

With reference to FIG. 10, a user may impatiently await the measurement while a preliminary value, in this case 20, is shown, as described above. If the preliminary value is acceptable to the user based on the user's clinical judgment, the user may accept it using the user input device 16 without waiting for completion of the measurement. For example, a user can select a menu item entitled "Accept preliminary value". With reference to FIG. 11, upon doing this, the preliminary value becomes the measured value and the prominent indicator 36 is replaced with the indicator 24 identifying the measured value, in this case 20. Further, the indicator 44 of the preliminary value is removed. The indicator 28 indicating whether the parameter is measured manually or automatically, and/or the indicator 30 indicating when the parameter is automatically measured, can be added to the window 22. Moreover, the indicator 32 indicating when the measurement completed, in this case 12:36, can be added to the window 22

Figure 12:
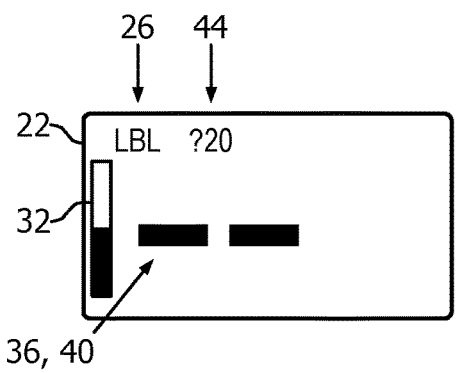

With reference to FIG. 12, when the indicator 44 identifying the preliminary value is displayed, the window 22 can also include an indicator 50 identifying one or more of the progress of the measurement, the stability of the estimate of the parameter, the quality (e.g., accuracy) of the estimate and/or the preliminary value, and the like. The indicator 50 can, for example, be text, a bar chart, and the like. As illustrated, this indicator 50 is a bar chart indicating that the accuracy of the estimate and/or the preliminary value is 50% (i.e., the likelihood of the estimate being correct is 50%). Advantageously, this indicator 50 can be used to enhance the confidence of users in accepting preliminary values.

Figure 13:
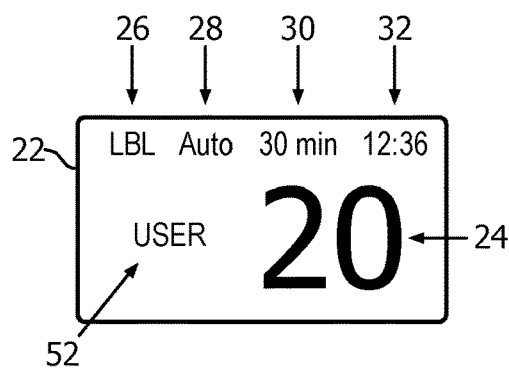
FIG. 13 illustrates a display including an indicator indicating how a measured value was accepted.

With reference to FIG. 13, upon completing a measurement, the window 22 can also include an indicator 52 identifying whether the measured value was automatically accepted or accepted by a user, as illustrated. A value is automatically accepted when the predetermined criteria for completing a measurement are met. A value is manually accepted when a user accepts a preliminary value.

Referring back to FIG. 1, the device 10 includes at least one processor 54 and at least one program memory 56. The program memory 56 includes processor executable instructions embodying the GUI 18 and which are executed by the processor 54 to carry out the above described functionality. The device 10 further includes a communication device 58 and at least one system bus. The communication device 58 allows the device 10 to communicate with external systems and/or devices, such as the external device and/or system. The system bus interconnects the processor 54, the program memory 56, the display device 20, the communication device 58, the user input device 16 and any other components of the device 10.

In view of the foregoing, the present invention describes an enhanced user interface which gives users clear and appropriate feedback dependent on the situation (i.e., a manually versus automatically triggered measurement). This, in turn, further reduces the potential of inadvertent user mistakes. Further, display of a preliminary value can help build confidence in a measurement and allow a user to judge early on if the measurement is progressing as expected. This, in turn, allows the user to early on accept the preliminary value or take corrective actions as the measurement is still ongoing. The foregoing advantages may save users time, especially while taking vital signs of many patients in a department during rounds.

While the foregoing only discussed a single parameter, it is to be appreciated that one or more additional parameters can be used with the GUI 18 for display and/or control of parameter measurement. For example, measurement of both NBP and temperature of a patient can be displayed and/or controlled using the GUI 18. Further, the GUI 18 is typically employed for aperiodic measurements (e.g., measurements which can be automatically and manually triggered) taking a prolonged period of time (e.g., more than 10 seconds).

As used herein, a memory includes one or more of: a non-transient computer readable medium; a magnetic disk or other magnetic storage medium; an optical disk or other optical storage medium; a random access memory (RAM), read-only memory (ROM), or other electronic memory device or chip or set of operatively interconnected chips; an Internet/Intranet server from which the stored instructions may be retrieved via the Internet/Intranet or a local area network; and the like. Further, as used herein, a processor includes one or more of a microprocessor, a microcontroller, a graphic processing unit (GPU), an application-specific integrated circuit (ASIC), an FPGA, and the like; a controller includes: (1) a processor and a memory, the processor executing computer executable instructions on the memory embodying the functionality of the controller; or (2) analog and/or digital hardware carrying out the functionality of the controller; a user input device includes one or more of a mouse, a keyboard, a touch screen display, a button, a switch, a voice recognition engine, and the like; a database includes one or more memories; a user output device includes a display device, a auditory device, and the like; and a display device includes one or more of a liquid crystal display (LCD) display, a light emitting diode (LED) display, a plasma display, a projection display, a touch screen display, and the like.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A medical device displaying data regarding measurement of a physiological parameter, said medical device comprising:
a display device; and
at least one processor programmed to:
display a window for the physiological parameter using the display device, the window including a third indicator identifying a measured value of the physiological parameter;
in response to an automatic trigger of measurement of the physiological parameter, update the window to further include a first indicator, having a first format and being static over time, indicating measurement of the physiological parameter is ongoing; and
in response to a manual trigger of measurement of the physiological parameter, update the window to replace the third indicator identifying the measured value with a second indicator, having a second format, indicating measurement of the physiological parameter is ongoing;
wherein the format of the second indicator is different from the format of the first indicator.

2. The medical device according to claim 1, wherein the second indicator is dynamic over time.

3. The medical device according to claim 1, wherein the at least one processor is further programmed to:
during an automatically triggered measurement of the physiological parameter, update the window to include an indicator identifying a preliminary value estimating the physiological parameter.

4. The medical device according to claim 3, wherein the at least one processor is further programmed to:
during the automatically triggered measurement of the physiological parameter, receive acceptance of the preliminary value;
in response to receiving acceptance of the preliminary value, end the automatically triggered measurement and update the window to replace the second indicator indicating measurement of the physiological parameter is ongoing with the indicator identifying the measured value, wherein the measured value is the preliminary value.

5. The medical device according to claim 3, wherein the at least one processor is further programmed to:
in response to the automatically triggered measurement failing to meet predetermined criteria within a predetermined amount of time, suspend the automatically triggered measurement and wait up to a predetermined amount of time for a user of the medical device to accept the preliminary value;
in response to failing to receive acceptance of the preliminary value within the predetermined amount of time, abort the automatically triggered measurement and update the window to replace the second indicator indicating measurement of the physiological parameter is ongoing with an indicator indicating the automatically triggered measurement was aborted.

6. The medical device according to claim 1, wherein the at least one processor is further programmed to:
automatically trigger measurement of the physiological parameter according to a timing sequence; and
in response to completion of a measurement of the physiological parameter, update the window include an indicator describing the timing sequence.

7. The medical device according to claim 1, wherein the at least one processor is further programmed to:

update the window to include an indicator indicating the stability and/or accuracy of a continuously refined estimate of the physiological parameter.

8. The medical device according to claim 1, wherein the at least one processor is further programmed to:
in response to completion of an automatically triggered measurement of the physiological parameter, update the window include an indicator indicating whether the measured value was accepted by a user of the device or met predetermined criteria for completing the automatically triggered measurement.

9. The medical device according to claim 1, wherein the first indicator is displayed with a smaller size than the second indicator.

10. The medical device according to claim 1, wherein the first indicator is displayed with a smaller size than the indicator identifying the measured value.

11. The medical device according to claim 1, wherein the at least one processor is further programmed to:
update the window to include the indicator identifying a preliminary value in response to a continuously refined estimate of the physiological parameter meeting predetermined criteria.

12. A medical method displaying data regarding measurement of a physiological parameter, said medical method comprising:
displaying a window for the physiological parameter using a display device, the window including a third indicator identifying a measured value of the physiological parameter;
in response to an automatic trigger of measurement of the physiological parameter, measuring the physiological parameter and continuing to display the third indicator identifying the measured value of the physiological parameter and updating the window to further include a first indicator indicating measurement of the physiological parameter is ongoing; and
in response to a manual trigger of measurement of the physiological parameter, measuring the physiological parameter and updating the window to replace the third indicator identifying the measured value with a second indicator indicating measurement of the physiological parameter is ongoing; wherein (i) the second indicator is dynamic over time and the first indicator is static over time and/or (ii) the second indicator is displayed with a larger size than the first indicator.

13. The medical method according to claim 12, further including:
during an automatically triggered measurement of the physiological parameter, updating the window to include an indicator identifying a preliminary value estimating the physiological parameter.

14. The medical method according to claim 13, further including:
during the automatically triggered measurement of the physiological parameter, receiving acceptance of the preliminary value;
in response to receiving acceptance of the preliminary value, ending the automatically triggered measurement and updating the window to replace the second indicator indicating measurement of the physiological parameter is ongoing with the indicator identifying the measured value, wherein the measured value is the preliminary value.

15. The medical method according to claim 13, further including:

in response to the automatically triggered measurement failing to meet, within a predetermined amount of time, predetermined criteria for completing the automatically triggered measurement, suspending the automatically triggered measurement and waiting up to a second predetermined amount of time for a user to accept the preliminary value;
in response to failing to receive acceptance of the preliminary value within the second predetermined amount of time, aborting the automatically triggered measurement and updating the window to replace the second indicator indicating measurement of the physiological parameter is ongoing with an indicator indicating the automatically triggered measurement was aborted.

16. The medical method according to claim 12, further including:
automatically triggering measurement of the physiological parameter according to a timing sequence; and
in response to completion of a measurement of the physiological parameter, updating the window include an indicator describing the timing sequence.

17. The medical method according to claim 12, further including:
update the window to include the indicator identifying a preliminary value in a response to a continuously refined estimate of the physiological parameter meeting predetermined criteria.

18. The medical method according to claim 12, further including:
update the window to include an indicator indicating the stability and/or accuracy of a continuously refined estimate of the physiological parameter.

19. A medical device displaying data regarding measurement of a physiological parameter, said medical device comprising:
a display device; and
at least one processor programmed to:
display a window for the physiological parameter using the display device, the window including a third indicator identifying a measured value of the physiological parameter;
in response to an automatic trigger of measurement of the physiological parameter, measure the physiological parameter and update the window to further include a first indicator, having a first format, indicating measurement of the physiological parameter is ongoing; and
in response to a manual trigger of measurement of the physiological parameter, measure the physiological parameter and update the window to replace the third indicator identifying the measured value with a second indicator, having a second format different from the format of the first indicator, indicating measurement of the physiological parameter is ongoing;
wherein the display device is configured to display
a graphical user interface (GUI) displaying data regarding measurement of a physiological parameter, said GUI comprising:
the window for the physiological parameter, the window including the third indicator;
wherein the window is updated to further include the first indicator indicating measurement of the physiological parameter is ongoing in response to the automatic trigger of measurement of the physiological parameter; and wherein the window is updated to replace the indicator identifying the measured value with the second indicator indicating measurement of the physiological parameter is ongoing in response to the manual trigger of measurement of the physiological parameter.

20. The medical device according to claim 19, wherein the window is updated to include the indicator identifying a preliminary value estimating the physiological parameter during an automatically triggered measurement of the physiological parameter; wherein acceptance of the preliminary value is referenced during the automatically triggered measurement of the physiological parameter; and wherein the automatically triggered measurement is ended, and the window is updated to replace the second indicator indicating measurement of the physiological parameter is ongoing with the indicator identifying the measured value, in response to receiving acceptance of the preliminary value, the measured value being the preliminary value.

* * * * *